(12) United States Patent
Morikis et al.

(10) Patent No.: US 9,751,097 B2
(45) Date of Patent: *Sep. 5, 2017

(54) TOPICAL SPRAY COMPOSITION TO BENEFIT SKIN

(71) Applicant: Conopco, Inc., Englewood Cliffs, NJ (US)

(72) Inventors: Thomas Nikolaos Morikis, Southington, CT (US); Kathleen Lynn Melo, Stratford, CT (US); Gee-Young Ng, New York, NY (US)

(73) Assignee: Conopco, Inc., Englewood Cliffs, NJ (US)

( * ) Notice: Subject to any disclaimer, the term of this patent is extended or adjusted under 35 U.S.C. 154(b) by 225 days.

This patent is subject to a terminal disclaimer.

(21) Appl. No.: 14/478,470

(22) Filed: Sep. 5, 2014

(65) Prior Publication Data

US 2014/0374508 A1 Dec. 25, 2014

Related U.S. Application Data

(63) Continuation of application No. 13/457,767, filed on Apr. 27, 2012, now Pat. No. 8,857,741.

(51) Int. Cl.
| | |
|---|---|
| *B05B 1/34* | (2006.01) |
| *B05B 11/00* | (2006.01) |
| *B65D 83/62* | (2006.01) |
| *A61K 8/04* | (2006.01) |
| *A61K 8/06* | (2006.01) |

(Continued)

(52) U.S. Cl.
CPC ............ *B05B 1/3405* (2013.01); *A61K 8/046* (2013.01); *A61K 8/06* (2013.01); *A61K 8/37* (2013.01); *A61K 8/375* (2013.01); *A61K 8/39* (2013.01); *A61K 8/86* (2013.01); *A61K 8/97* (2013.01); *A61Q 19/00* (2013.01); *B05B 1/3426* (2013.01); *B05B 11/0037* (2013.01);

(Continued)

(58) Field of Classification Search
CPC ..... B05B 1/3405; B05B 1/341; B05B 1/3421; B05B 1/3426; B05B 11/0037; A61K 8/046; A61K 8/06; A61K 8/37; A61K 8/375; A61K 8/39; A61K 8/86; A61K 8/97; A61K 2800/10; A61K 2800/87; A61Q 19/00; A61Q 19/04; A61Q 19/08; B65D 83/62

See application file for complete search history.

(56) References Cited

U.S. PATENT DOCUMENTS

| | | |
|---|---|---|
| 4,844,902 A | 7/1989 | Grohe |
| 5,753,244 A | 5/1998 | Reynolds et al. |

(Continued)

FOREIGN PATENT DOCUMENTS

| | | |
|---|---|---|
| AU | 2009202123 | 12/2009 |
| BE | 865222 | 9/1978 |

(Continued)

OTHER PUBLICATIONS

Search Report and Written Opinion in EP16150298, Feb. 29, 2016.

(Continued)

*Primary Examiner* — Darren W Gorman
(74) *Attorney, Agent, or Firm* — Edward A. Squillante, Jr.

(57) ABSTRACT

A topical spray composition and a system for containing and applying the composition is described. The composition has liquid emulsifiers that unexpectedly result in a superior product suitable to be applied homogeneously.

14 Claims, 1 Drawing Sheet

(51) Int. Cl.
*A61Q 19/00* (2006.01)
*A61K 8/39* (2006.01)
*A61K 8/86* (2006.01)
*A61K 8/37* (2006.01)
*A61K 8/97* (2017.01)
*A61Q 19/04* (2006.01)
*A61Q 19/08* (2006.01)

(52) U.S. Cl.
CPC .......... *B65D 83/62* (2013.01); *A61K 2800/10* (2013.01); *A61K 2800/87* (2013.01); *A61Q 19/04* (2013.01); *A61Q 19/08* (2013.01)

(56) References Cited

U.S. PATENT DOCUMENTS

| | | |
|---|---|---|
| 5,989,529 A | 11/1999 | Kaplan |
| 5,997,888 A | 12/1999 | Weder et al. |
| 6,007,797 A | 12/1999 | Bell et al. |
| 6,290,936 B1 | 9/2001 | Ross et al. |
| 6,332,563 B2 | 12/2001 | Baudin |
| 6,423,326 B1 | 7/2002 | Shapiro |
| 6,586,479 B2 | 7/2003 | Miller et al. |
| 6,620,420 B2 | 9/2003 | Lanzendorfer et al. |
| 6,667,044 B1 | 12/2003 | Diec et al. |
| 6,685,109 B2 | 2/2004 | Py |
| 7,074,747 B1 | 7/2006 | Lukenbach et al. |
| 7,078,046 B1 | 7/2006 | Rabe et al. |
| 7,094,448 B2 | 8/2006 | Ono et al. |
| 7,282,196 B2 | 10/2007 | Kux et al. |
| 7,323,507 B2 | 1/2008 | Loffler et al. |
| 7,481,996 B2 | 1/2009 | Ishii et al. |
| 7,615,586 B2 | 11/2009 | Moreno |
| 7,645,804 B2 | 1/2010 | Rossow et al. |
| 7,964,201 B2 | 6/2011 | Bertz et al. |
| 2001/0011687 A1 | 8/2001 | Benoist |
| 2002/0155076 A1 | 10/2002 | Lanzendorfer et al. |
| 2002/0176832 A1 | 11/2002 | Lanzendorfer et al. |
| 2003/0219398 A1 | 11/2003 | Loeffler et al. |
| 2004/0037797 A1 | 2/2004 | Nielsen et al. |
| 2004/0081629 A1 | 4/2004 | Meyer et al. |
| 2004/0105873 A1 | 6/2004 | Gupta |
| 2004/0253187 A1 | 12/2004 | Kux et al. |
| 2005/0124705 A1 | 6/2005 | Schreiber et al. |
| 2005/0163812 A1 | 7/2005 | Hoath et al. |
| 2005/0186236 A1 | 8/2005 | Dorschner et al. |
| 2005/0201003 A1 | 9/2005 | Shishida et al. |
| 2005/0208003 A1 | 9/2005 | Gupta |
| 2005/0238680 A1 | 10/2005 | Stella et al. |
| 2005/0239670 A1 | 10/2005 | Stella et al. |
| 2006/0111490 A1 | 5/2006 | Fonolla Moreno |
| 2006/0135383 A1 | 6/2006 | Cossa et al. |
| 2006/0210497 A1 | 9/2006 | Harichian et al. |
| 2006/0233720 A1 | 10/2006 | Stork et al. |
| 2006/0270743 A1 | 11/2006 | Rossow |
| 2007/0108228 A1 | 5/2007 | Kleyne |
| 2007/0190012 A1 | 8/2007 | Feng et al. |
| 2007/0276033 A1 | 11/2007 | Gupta |
| 2008/0031845 A1 | 2/2008 | Stella |
| 2008/0085252 A1 | 4/2008 | Van et al. |
| 2009/0324506 A1 | 12/2009 | Seidling et al. |
| 2010/0116909 A1 | 5/2010 | Abduljalil |
| 2010/0219211 A1 | 9/2010 | Smith et al. |
| 2010/0278906 A1 | 11/2010 | Sondgeroth et al. |
| 2011/0057057 A1 | 3/2011 | Songbe |
| 2011/0059032 A1 | 3/2011 | Dierker et al. |
| 2011/0139810 A1 | 6/2011 | Lee |
| 2011/0158922 A1 | 6/2011 | Dupont et al. |
| 2012/0234947 A1* | 9/2012 | Takahashi .......... B05B 1/02 239/601 |

FOREIGN PATENT DOCUMENTS

| | | |
|---|---|---|
| CN | 1366874 | 9/2002 |
| CN | 1558799 | 12/2004 |
| CN | 101522311 | 9/2009 |
| DE | 10063659 | 7/2002 |
| DE | 10245727 | 4/2004 |
| DE | 10344888 | 4/2005 |
| EP | 1247519 | 10/2002 |
| EP | 1557153 | 7/2005 |
| EP | 1577361 | 9/2005 |
| EP | 1474099 | 9/2009 |
| EP | 1555017 | 12/2009 |
| EP | 2033617 | 10/2010 |
| EP | 1438009 | 7/2014 |
| GB | 2113706 | 9/1985 |
| JP | 4502441 | 5/1992 |
| JP | 3047587 | 4/1998 |
| JP | 11171269 | 6/1999 |
| JP | 2001114639 | 4/2001 |
| JP | 2001213488 | 8/2001 |
| JP | 2002519193 | 7/2002 |
| JP | 2004107226 | 4/2004 |
| JP | 2008266275 | 11/2008 |
| JP | 2008540091 | 11/2008 |
| JP | 2009292734 | 12/2009 |
| JP | 201037200 | 2/2010 |
| JP | 2011514338 | 5/2011 |
| JP | 4782634 | 9/2011 |
| KR | 20020026391 | 4/2002 |
| KR | 20090014413 | 2/2009 |
| KR | 20100030432 | 3/2010 |
| KR | 20100085435 | 7/2010 |
| KR | 20100093223 | 8/2010 |
| KR | 20100136154 | 12/2010 |
| KR | 20110051880 | 5/2011 |
| WO | W09005580 | 5/1990 |
| WO | WO9815254 | 4/1998 |
| WO | W00001493 | 1/2000 |
| WO | WO0243686 | 6/2002 |
| WO | WO03022237 | 3/2003 |
| WO | WO2004000248 | 3/2004 |
| WO | WO2004030641 | 4/2004 |
| WO | WO2006045583 | 5/2006 |
| WO | W02006127362 | 11/2006 |
| WO | WO2008045582 | 4/2008 |
| WO | WO2009083131 | 8/2009 |
| WO | W02009108713 | 9/2009 |
| WO | WO2010121884 | 10/2010 |
| WO | WO2011069674 | 6/2011 |
| WO | WO2011126978 | 10/2011 |

OTHER PUBLICATIONS

3 Cans Rite Aid Renewal Daily Moisturizing continuous Spray Skin Protect 6 oz Ea, Ebay, Mar. 4, 2014, 1-2.
Rite Aid Renewal Daily Moisturizing—Directions for Me, Directions for me, 2014, 1-3.
Search Report in PCTEP2013058466, May 27, 2014.
Written Opinion in PCTEP2013058466, May 27, 2014.
Written Opinion 2 in PCTEP2013058466, Sep. 17, 2014.
Aftersun Foam Spray, Mintel GNPD, May 2008.
Body Oil Spray, Mintel GNPD, Aug. 1996.
Classic, Mintel GNPD, Aug. 1996.
L-C Soften Moisturising Spray, Mintel GNPD, Jul. 2002.
Moirsutirisng Body Spray, Mintel GNPD, Nov. 2010.
Moisturiser, Mintel GNPD, Aug. 1997.
Moisturizing Microfine Mist, Mintel GNPD, Mar. 2007.
Oat Water Moisturiser, Mintel GNPD, Nov. 2008.
Palmers Aloe Vera Formula, Mintel GNPD, Nov. 1996.
Polo Sport Woman, Mintel GNPD, May 1997.
Skin Care Products, Mintel GNPD, Mar. 1997.
Skin-So-Soft Spray-On Moisturizing Body Lotion, Mintel GNPD, Aug. 1997.
IPRP2 in PCTEP2013058466, Nov. 27, 2014.
Picture Rite Aid Product With Ingredient list, Apr. 11, 2011, pp. 1-2.

* cited by examiner

TOPICAL SPRAY COMPOSITION TO BENEFIT SKIN

This application is a continuation of U.S. Ser. No. 13/457,767 filed Apr. 27, 2012.

FIELD OF THE INVENTION

The present invention is directed to a topical spray composition for delivering benefit agents to skin. More particularly, the invention is directed to a topical spray composition that comprises a substantially all liquid emulsification system that has a HLB from about 3.0 to about 7.0. The spray composition is surprisingly stable and capable of being applied homogeneously (i.e., not blotchy or patchy) to skin. Moreover, the system for delivering the spray composition is one which not only ensures homogenous application with a desirable spray pattern but also unexpectedly allows for product application in the absence of sputtering and mess.

BACKGROUND OF THE INVENTION

The human skin is man's largest organ. The prominent roles of skin are to protect the body and guide the body as its main sensory organ. The condition of our skin greatly affects how we look and feel. Caring for one's skin is, therefore, a relevant consumer concern.

Topical compositions have long been used to deliver benefits to consumers. Such benefits can be pharmaceutical and/or cosmetic in nature.

Ointments, for example, have served as emollients and mainly for medicinal purposes by acting as carriers for pharmaceuticals, drugs and the like. Ointments deliver such components to the body after being topically applied.

Personal care products such as creams, lotions, pastes and gels are also commonly employed to deliver benefit agents to skin of consumers. Via topical application, the same are applied to skin to yield benefits such as skin lightening, sun protection and moisturization.

While ointments, lotions and creams, for example, are known and widely accepted vehicles for delivering skin benefit agents, these vehicles can be difficult (and time consuming) to apply. In fact, many consumers avoid caring for their skin for the sole reason that they refuse to take the time to apply a composition, like a lotion, to the body.

There is an increasing interest to develop an easy to apply topical composition that is consumer friendly and not time consuming to apply. Moreover, there is an increasing interest to develop an easy to apply composition that is stable and suitable to be delivered in a desirable spray pattern in order to provide results that are beneficial to skin. This invention, therefore, is directed to a superior topical spray composition for delivering such results. The topical spray composition of this invention comprises a substantially all liquid emulsification system that has an HLB from about 3.0 to about 7.0. The spray composition is surprisingly stable, notwithstanding the low HLB emulsification system employed, and capable of being applied homogeneously to skin. Moreover, the system for delivering the spray composition yields a desirable and continuous spray pattern in the absence of sputtering as well as a composition suitable to be quickly absorbed into skin.

ADDITIONAL INFORMATION

Efforts for making topical compositions have been disclosed. In U.S. Patent Application Nos. 2004/105873 A1, 2005/208003 A1 and 2007/276033 A1, topical formulations with water and oil soluble ingredients are disclosed.

Other efforts have been disclosed for making topical compositions. In U.S. Pat. No. 6,620,420 B2, gel creams, in the form of emulsions containing ammonium acryloyldimethyltaurate/vinylpyrrolidone copolymers are described.

Even other efforts have been disclosed for making topical skin compositions. In U.S. Pat. No. 5,753,244, skin treatments and ointments are described.

Still further, additional efforts have been disclosed for making topical compositions. In U.S. Patent Application No. 2006/0210497 A1, compositions with novel resorcinol derivatives are described.

None of the additional information above describes a topical spray composition as well as a spray system for delivering the same as claimed in this invention.

SUMMARY OF THE INVENTION

In a first aspect, the present invention is directed to a composition comprising:
  a) liquid emulsifier, the liquid emulsifier having an HLB from about 3.0 to about 7.0; and
  b) skin benefit agent
wherein the composition is sprayable, has a viscosity from about 500 to about 4200 cps and a surface tension from about 22 to about 33 mN/m.

In a second aspect, the present invention is directed to a system comprising:
  a) a package with a headspace of about 30 to 55% and capable of being pressurized to 75 to 155 psi;
  b) an exit insert, the exit insert having at least one channel, swirl chamber and orifice; and
  c) the composition of the first aspect of this invention
wherein the swirl chamber has a diameter from about 0.5 mm to about 2.0 mm, the orifice has a diameter from about 0.15 mm to about 0.4 mm and the channel has a length from about 3 to about 9 times larger than the orifice diameter and a width from about 0.7 to about 5 times longer than the orifice diameter and further wherein the orifice diameter to swirl chamber diameter (d/D) is less than 0.45.

All other aspects of the present invention will more readily become apparent upon considering the detailed description and examples which follow.

Figure 1:
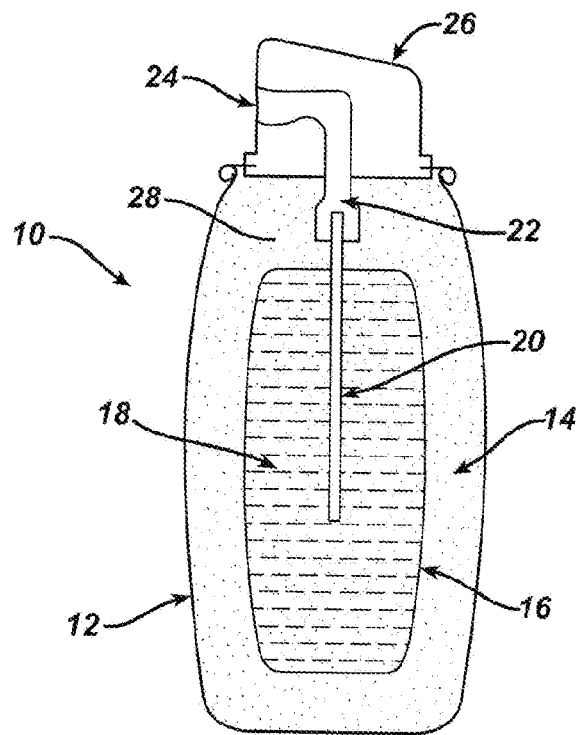
FIG. 1 shows a sectional view of an illustrative bag on valve package suitable for use in this invention.

Topical, as used herein, means external to the body. Skin, as used herein, is meant to include skin on the face, neck, chest, back, arms (including underarms), hands, legs, feet, buttocks and scalp. Air, as used herein, means a gas like, for example, nitrogen, atmospheric gas, inert gas such as argon, or a gas having at least oxygen in combination with carbon dioxide, water vapor and/or nitrogen. Skin benefit agent means an agent applied topically and suitable to be formulated in a sprayable composition, the skin benefit agent being one that, for example, diverts UVA and/or UVB sunlight, moisturizes, artificially colors, lightens and/or reduces wrinkles on skin.

Substantially free of means less than 0.5%, and preferably, from about 0.001 to about 0.3% by weight in the composition and based on total weight of the composition. In an especially preferred embodiment, the composition of this invention is substantially free of non-liquid emulsifier. In a most especially preferred embodiment, no (0.0% by weight) non-liquid emulsifier will be used in the composition of this invention. Environmentally friendly means being at least substantially free of non-liquid emulsifier, as well as organic propellants.

Stable, as used herein, means suitable for homogeneous spraying for no less than three months when stored at room temperature. The composition of this invention can be leave-on or wash-off but is preferably a leave-on composition. Viscosity is taken on a Brookfield Viscometer (speed at 20 rpm, spindle 5, helipath off, and for one (1) minute at ambient temperature). Surface tension is measured on a commercially available instrument such as those sold by Krüss USA. The method used for determining surface tension is one typically called the Ring Method. Continuous spray means spraying with one (1) actuator button depression and not via a pump.

Comprising, as used herein, is meant to include consisting essentially of and consisting of. For the avoidance of doubt and by way of illustration, the composition of this invention can consist essentially of liquid emulsifier, skin benefit agent, air, and minors, or the composition of this invention can consist of the same. Minors, as used herein, means typical ingredients for perfecting topical compositions such as perfecting the same for end use without having an impact on intended benefit. Minors can include, for example, preservatives, fragrances, colorants (like iron oxides), pH buffers, visual additives like speckles and/or the like. Emulsion includes a composition with water and oil, and preferably, a water-in-oil or oil-in-water emulsion. In a most preferred embodiment, the emulsion of this invention is oil-in-water. All ranges identified herein are meant to include all ranges subsumed therein if, for example, reference to the same is not explicitly made.

DETAILED DESCRIPTION OF THE PREFERRED EMBODIMENTS

The only limitations with respect to the liquid emulsifiers that may be used in this invention are that the emulsifiers have an HLB from about 3.0 to about 7.0 and are suitable for use on compositions topically applied to humans.

Illustrative examples of the types of liquid emulsifiers suitable for use herein include those generally classified as non-polymeric, polyhydroxylated fatty acid esters, polymeric, polyhydroxylated fatty acid esters or mixtures thereof.

Illustrative yet non-limiting examples of the types of non-polymeric, polyhydroxylated fatty acid esters suitable for use in this invention include sorbitan isostearate, sorbitan monooleate, glycerol isostearate, methylglucoside sesquistearate, sorbitan diisostearate, sorbitan sesquioleate, mixtures thereof or the like. With respect to the polymeric, polyhydroxylated fatty acid esters suitable for use, illustrative examples include polyglyceryl-3-diisostearate, polyglyceryl-3-polycrinoleate, polyethylene glycol-4 dilaurate, polyethylene glycol-4 dioleate, polyethylene glycol-30 dipolyhydroxystearate, mixtures thereof or the like.

In an especially preferred embodiment, both non-polymeric, polyhydroxylated fatty acid esters and polymeric, polyhydroxylated fatty acid esters are used in the liquid emulsifier system wherein from about 2 to about 8, and preferably, from about 3 to about 8, and most preferably, from about 5 to about 7 times more of the nonpolymeric emulsifier is used than the polymeric emulsifier, based on total weight of total emulsifier in the composition, and including all ranges subsumed therein. In a most especially preferred embodiment, the nonpolymeric, polyhydroxylated fatty acid emulsifier used in this invention is sorbitan isostearate and the polymeric, polyhydroxylated fatty acid emulsifier is polyglyceryl-3-diisostearate.

With respect total amount of liquid emulsifier used in the compositions of this invention, typically from about 1.5 to about 6.0, and preferably, from about 2 to about 5, and most preferably, from about 2.75 to about 4.0 percent by weight liquid emulsifier is used, including all ranges subsumed therein.

The HLB of the liquid emulsification system in this invention is often, from about 3 to about 7, and preferably, from about 3.5 to about 6.5, and most preferably, from about 3.5 to about 5.5, including all ranges subsumed therein.

The topical spray compositions of the present invention will typically include cosmetically acceptable carriers. Water is the most preferred carrier. Amounts of water may range from about 45 to about 99%, and preferably, from about 70 to about 98%, and most preferably, from about 75 to about 96% and optimally from about 77 to about 90% by weight, based on total weight of the spray composition and including all ranges subsumed therein. Ordinarily, the compositions will be water and oil emulsions. As previously mentioned, most preferably, are the oil-in-water type emulsions.

Other cosmetically acceptable carriers suitable for use in the spray compositions of this invention may include mineral oils, silicone oils, synthetic or natural esters, fatty acids and alcohols. Amounts of these materials may range from about 0.5 to about 12%, and preferably, from about 0.5 to about 10%, and most preferably, from about 1 to about 8% by weight of the spray composition, including all ranges subsumed therein.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, and preferably, from about 4 to about 5 silicon atoms.

Linear volatile silicone materials generally have viscosities of less than about 5 centistokes at 25° C. while cyclic materials typically have viscosities of less than about 10 centistokes.

Nonvolatile silicone oils useful as carrier material include polyalkyl siloxanes, polyalkylaryl siloxanes and polyether siloxane copolymers. The essentially non-volatile polyalkyl siloxanes useful herein include, for example, polydimethylsiloxanes (like dimethicone) with viscosities of from about 5 to about 100,000 centistokes at 25° C.

An often preferred silicone source is a cyclopentasiloxane and dimethiconol solution.

Among suitable esters are:
(1) Alkenyl or alkyl esters of fatty acids having 10 to 20 carbon atoms like isopropyl palmitate, isopropyl isostearate, isopropyl myristate, isononyl isononanoate, oleyl myristate, oleyl stearate, and oleyl oleate;
(2) Ether-esters such as fatty acid esters of ethoxylated fatty alcohols;
(3) Polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters;

(4) Wax esters such as beeswax, spermaceti, myristyl myristate, stearyl stearate; and (5) Sterol esters, of which soya sterol and cholesterol fatty acid esters are examples thereof.

Fatty acids having from 10 to 30 carbon atoms may be included in the spray compositions of this invention. Illustrative of this category are pelargonic, lauric, myristic, palmitic, stearic, isostearic, hydroxystearic, oleic, linoleic, ricinoleic, arachidic, behenic and erucic acids.

Optionally, surfactant may be used in the spray compositions of the present invention. These include glyceryl stearate, glycol stearate, stearamide AMP, PEG-100 stearate, cetyl alcohol as well as emulsifying/thickening additives like hydroxyethylacrylate/sodium acryloyldimethyl taurates copolymer/squalane and mixtures thereof. When used, surfactant typically makes up less than 0.45% by weight of the spray composition. Surfactant, if used, more typically makes up from about 0.001 to about 0.4% by weight of the spray composition.

Preservatives can desirably be incorporated into the spray compositions comprising the liquid emulsification system of this invention to protect against the growth of potentially harmful microorganisms. Suitable traditional preservatives for the spray compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the spray compositions. Preservatives are preferably employed in amounts ranging from about 0.01% to about 2% by weight of the spray composition, including all ranges subsumed therein.

Thickening agents may be included in the spray compositions of the present invention. Particularly useful are the polysaccharides. Examples include starches, natural/synthetic gums and cellulosics. Representative of the starches are chemically modified starches such as sodium hydroxypropyl starch phosphate and aluminum starch octenylsuccinate. Tapioca starch is often preferred. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are yet another class of effective thickening agent. This category includes crosslinked polyacrylates such as the Carbomers such as Carbopol Ultrez® 10, polyacrylamides such as Sepigel® 305 and taurate copolymers such as Simulgel EG® and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel INS100.

Amounts of the thickener may range from about 0.001 to about 3.5%, and preferably, from about 0.01 to about 2%, and most preferably, from about 0.1 to about 0.7% by weight of the composition including all ranges subsumed therein.

Often preferred minors suitable for use include aloe vera (leaf juice powder) cocoa butter, oat/straw extract, colorants and/or fragrances. These may optionally be included either alone or in mixtures in the spray composition of this invention. Each of these substances may range from about 0.001 to about 4%, preferably they collectively make up between 0.01 to about 3% by weight of the total weight of the spray composition, including all ranges subsumed therein.

To enhance skin moisturization, cationic ammonium compounds may optionally be used in the spray compositions of this invention. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono (hydroxyethyl) ammonium salts, guar hydroxypropyl trimonium salts, 2,3-dihydroxypropyl tri($C_1$-$C_3$ alkyl or hydroxalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from about 0.001 to about 15%, and preferably, from about 0.01 to about 5%, and most preferably, from about 0.01 to about 2% by weight of the composition.

When cationic ammonium compounds are used, preferred additives for use with the same are moisturizing agents such as substituted ureas like hydroxymethyl urea, hydroxyethyl urea, hydroxypropyl urea; bis(hydroxymethyl)urea; bis(hydroxyethyl)urea; bis(hydroxypropyl)urea; N,N'-dihydroxymethyl urea; N,N'-di-hydroxyethyl urea; N,N'-di-hydroxypropyl urea; N,N,N'-tri-hydroxyethyl urea; tetra (hydroxymethyl)urea; tetra(hydroxyethyl)urea; tetra (hydroxypropyl)urea; N-methyl-N'-hydroxyethyl urea; N-ethyl-N,N-N'-hydroxyethyl urea; N-hydroxypropyl-N'-hydroxyethyl urea and N,N'-dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea, when used, in the composition of this invention range from about 0.001 to about 10%, and preferably, from about 0.01 to about 5%, and most preferably, from about 0.01 to about 1.0%, based on total weight of the spray composition and including all ranges subsumed therein.

Conventional humectants may be employed in the present invention. These are generally polyhydric alcohol-type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.5 to 20%, preferably between 1 and 7%, and most preferably, from about 1 to about 5% by weight of the composition.

When cationic ammonium compound is used, in a most especially preferred embodiment at least from about 1 to about 12% by weight glycerin is used, based on total weight of the spray composition and including all ranges subsumed therein.

As illustrative skin benefit agents, the topical spray compositions of the present invention may include vitamins. Illustrative vitamins are Vitamin A (retinol), retinol esters (like retinol palmitate and/or retinol propionate, Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 5%, preferably from 0.01% to 2%, optimally from 0.1 to 1% by weight of the spray composition.

Other illustrative skin benefit agents include octadecendioic acid, azelaic acid, ubiquinone, dihydroxyacetone (sunless tanning agent), mixtures thereof or the like. These agents typically make up from about 0.5 to about 4% by weight of the total weight of the spray composition when they are used.

Even other skin benefit agents suitable for use include resveratrol, resorcinols like 4-ethyl resorcinol, 4-hexyl resorcinol, 4-phenylethyl resorcinol, dimethoxytoluyl propyl resorcinol, 4-cyclopentyl resorcinol, 4-cyclohexylresorcinol, alpha-an/or beta-hydroxyacids, petroselinic acid, conjugated linoleic acid, octadecanoic acid, phenylethyl resorcinol (Symwhite 377 from Symrise), undecylenol phenylalanine (Seppi White from Seppic) mixtures thereof or the like. Such agents, when used, collectively make up from about 0.001 to about 8% by weight of the spray composition.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials, when optionally present, may range from about 0.01 to about 5% by weight of the composition.

A variety of extracts may optionally be included in compositions of this invention in addition to previously described oat/straw extracts. Additional illustrative extracts suitable for use include those from green tea, yarrow, chamomile, licorice, aloe vera, grape seed, citrus unshui, willow bark, sage, thyme and rosemary.

Also optionally suitable for use include materials like sunscreens as well as lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 5%, preferably from about 0.0001 to about 1.5% by weight of the spray composition.

When used, often preferred sunscreens (i.e., skin benefit agents) include phenylbenzimidazole sulfonic acid (Ensulizole), ethylhexyl p-methoxycinnamate, available as Parsol MCX®, Avobenzene, available as Parsol 1789® and benzophenone-3, also known as Oxybenzone. Inorganic sunscreen actives may be employed such as microfine titanium dioxide, zinc oxide, polyethylene and various other polymers. Also suitable for use is octocrylene.

Conventional buffers/pH modifiers may be used. These include commonly employed additives like sodium hydroxide, hydrochloric acid, citric acid and citrate/citric acid buffers. In an especially preferred embodiment, the pH of the composition of this invention is from about 3 to about 8.5, and preferably, from about 4.0 to about 8.0, and most preferably, from about 4.5 to about 7.0, including all ranges subsumed therein.

Opacifiers and chelators (like tetrasodium EDTA) may also be included in the compositions of the present invention. Each of these substances may range from about 0.01 to about 5%, preferably between 0.01 and 2% by weight of the topical spray composition when they are used.

The preparation of the topical spray composition of this invention is typically achieved by combining and mixing the preferred ingredients under conditions of atmospheric pressure, temperature at ambient to about 80° C. and moderate shear in a conventional mixing vessel.

In a preferred embodiment, the viscosity of the spray composition of this invention is from about 600 to about 4000 cps, and most preferably, from about 1200 to about 3500 cps, including all ranges subsumed therein.

The surface tension of the spray composition is preferably from about 25 to about 32 MN/m, and most preferably, from about 28 to about 32 MN/m, including all ranges subsumed therein.

Turning to the figures, FIG. 1 depicts a cross section of a bag on valve package 10 preferred for use with the topical spray composition used in the system of this invention. The container 12 is internally pressurized with air 14 preferably from about 90 to 140 psi, and most preferably, from about 100 to about 135 psi, including all ranges subsumed therein. Bag, 16 contains or holds topical spray composition of this invention 18 for elimination and use through tube 20 and tube connector 22 through exit insert 24 housed in actuator cap 26 that operative allows for composition 18 to exit the exit insert 24 upon pressing button (not shown) in actuator cap 26 to engage conventional bag on valve package mechanics (not shown).

The package 10, preferably has a headspace 28 that accounts for from about 35 to about 50%, and preferably, from about 37 to about 45% by volume of the package 10.

Figure 2:
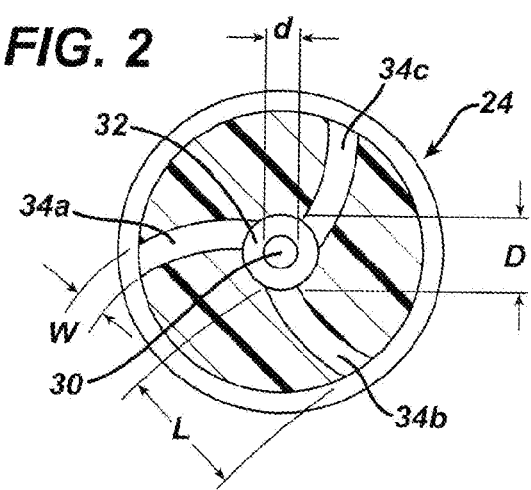
FIG. 2 shows a front view of an illustrative exit insert suitable for use in this invention.

Turning to FIG. 2, shown is a rear elevated view of exit insert 24 having an orifice 30 surrounded by swirl chamber 32 operatively connected to channels 34a-c (preferably, 2 to 4, and most preferably, 2 to 3 channels are desired for this invention) for feeding topical spray composition 18 from tube connector 22 to swirl chamber 32 and out through orifice 30 generally centrally position in exit insert 24.

In a preferred embodiment, the swirl chamber 32 has a diameter, D, that is from about 0.6 to about 1.7 mm, and preferably, from about 0.8 to about 1.2 mm, including all ranges subsumed therein. The orifice preferably has a diameter, d, from about 0.2 to about 0.35 mm, and most preferably, from about 0.25 to 0.30 mm, including all ranges subsumed therein.

The channels 34a-c preferably have a length, L, that is 3.5 to 8, and most preferably, from 3.8 to 7 times longer than the orifice diameter, d. The width, W, of the channels 34a-c is preferably from about 0.7 to about 4, and most preferably, from about 1.2 to about 3 times longer than the orifice diameter, d. it is within the scope of this invention for the width, W, of the channels 34a-c to be uniform as shown or somewhat tapered (not shown).

In a preferred embodiment, d/D is from about 0.25 to about 0.4, and preferably, from about 0.27 to about 0.39, including all ranges subsumed therein.

Component parts of the packaging 10, including can or container and exit insert, described herein, are made commercially available. Suppliers like Calmar or Mead West Vaco, Aptar Group, Inc., and Lindal NA, Inc. are often preferred sources. The packaging 10 is typically a metal or metal alloy, preferably one prepared from recycled materials.

Surprisingly, it has been discovered that when applying (the method of using) the topical spray composition from the system of this invention, a superior and homogeneous spray pattern is achieved such that when applying product from about 10 to about 15 cm from a substrate (e.g., hands, legs, arms) a continuous product application pattern of about 4 to 8 cm in width and from about 2.5 to about 10 cm, and preferably, from about 2.5 to about 9 cm, and most preferably, from about 3.5 to about 8 cm in length is generated. Such a pattern of spray composition requires little composition rubbing from the consumer for excellent absorption. Moreover, such a pattern is controlled, reliable and does not yield a mess upon application. Such a product application pattern makes the method of using the system of this invention very desirable for a consumer, especially one with little time.

The system of this invention not only results in a superior product application pattern, the same results in a spray rate of 0.8 to 2 g, preferably, from 1 to 1.6 g of product release or application per second of spraying from package 10. Such a product results in excellent skin benefits to consumers typically not willing to use conventional lotions that often are messy and time consuming to apply.

The following examples are provided to facilitate an understanding of the present invention. The examples are not intended to limit the scope of the claims.

Example 1

The ingredients below were combined and mixed with moderate shear in a conventional mixing chamber operating under conditions of atmospheric pressure and at a temperature of about 75° C. Produced were three (3) variants of topical spray composition consistent with this invention.

| Ingredient | Composition 1 % w/w | Composition 1 % w/w | Composition 1 % w/w |
| --- | --- | --- | --- |
| Glycerin | 3.50 | 3.50 | 3.50 |
| Isopropyl Myristate | 7.00 | 7.00 | 7.00 |
| Disodium EDTA | 0.05 | 0.05 | 0.05 |
| Preservative | 0.7 | 0.7 | 0.7 |
| Deionized Water | Balance | Balance | Balance |
| Stearic Acid | 0.10 | 0.10 | 0.10 |
| Dihydroxypropyltrimonium Chloride | 0.10 | 0.10 | 0.10 |
| Sodium Hydroxide | 0.05 | 0.05 | 0.05 |
| Sorbitan Isostearate | 3.00 | 3.00 | 3.00 |
| Polyglyceryl 3-diisostearate | 0.50 | 0.50 | 0.50 |
| Dimethicone | 3.00 | 3.00 | 3.00 |
| Thickener | 0.57 | 0.57 | 0.57 |
| Fragrance | 0.15 | 0.15 | 0.15 |
| (OAT) Straw Extract | 0.01 | — | — |
| Theobroma cacao (cocoa) seed butter | — | — | 0.01 |
| Aloe extract | — | 0.01 | — |
|  | 100.00 | 100.00 | 100.00 |

Example 2

The compositions of Example 1 were filled into commercially available bag on valve packages as described in this invention. The packages were filled and pressurized to about 120 psi. Skilled panelists applied the product (about two (2) seconds of spraying, three (3) grams of product) to their forearms from about a 10 cm distance from their arms. All panelists unanimously concluded that the system of this invention generated an excellent and homogeneous product in a desirable pattern. The panelists also concluded that the product delivered in this invention and from the inventive system was faster and easier to apply than a conventional lotion, wherein the composition absorbed into their skin easily with limited amount of rubbing.

Example 3

The compositions in the inventive systems prepared in Example 1 were sprayed onto different areas of a vertical substrate from a distance of about 10 cm (about three (3) grams of product as described in Example 2). The compositions were compared to commercially sold spray moisturizer (comprising solid emulsifier) also applied in the same manner to the vertical substrate. All panelists concluded that the spray compositions applied via the system of this invention were more even and controlled and did not display any product running after about thirty (30) minutes from application. The commercially sold product, control with solid emulsifier, did run significantly on application.

What is claimed is:

1. A system comprising:
   a) a package with a headspace of 30 to 55% based on volume of the package and capable of being pressurized to 5.2 to 10.7 bar;
   b) an exit insert, the exit insert having at least one channel, a swirl chamber and an orifice; and
   c) a composition comprising:
      i) a liquid emulsifier, the liquid emulsifier having an HLB from 3.0 to 7.0; and
      iii) a skin benefit agent, the composition is sprayable from the system at a spray rate of 0.8 to 2 g per second, has a viscosity from 500 to 4200 cps and a surface tension from 22 to 33 mN/m
   wherein the swirl chamber has a diameter, D, from 0.5 mm to 2.0 mm, the orifice has a diameter, d, from 0.15 mm to 0.4 mm, and the at least one channel has a length from 3.0 to 9 times larger than the orifice diameter, and a width from 0.7 to 5 times longer than the orifice diameter and further wherein the ratio of the orifice diameter to the swirl chamber diameter (d/D) is less than 0.45.

2. The system according to claim 1 wherein the liquid emulsifier comprises a non-polymeric, polyhydroxylated fatty acid, a polymeric, polyhydroxylated fatty acid, or both.

3. The system according to claim 1 wherein the ratio (d/D) is from 0.25 to 0.4.

4. The system according to claim 1 wherein the composition is sprayable from the system at a spray rate of 1 to 1.6 g per second.

5. The system according to claim 1 wherein the composition is sprayable from the system in a homogeneous spray pattern.

6. The system according to claim 1 wherein the composition is sprayable from the system in a pattern of about 2.5 to 10 cm in width.

7. The system according to claim 1 wherein the orifice has a diameter from about 0.2 to about 0.35 mm.

8. The system according to claim 1 wherein the swirl chamber has a diameter from about 0.6 to about 1.7 mm.

9. The system according to claim 1 wherein the emulsifier in the composition consists essentially of liquid emulsifier.

10. The system according to claim 1 wherein the composition is an oil-in-water emulsion comprising from about 70% to about 98% water.

11. The system according to claim 1 wherein the composition comprises from about 0.5% to about 12% by weight oil.

12. The system according to claim 1 wherein the composition comprises less than 0.5% by weight non-liquid emulsifier.

13. The system according to claim 1 wherein the composition comprises less than 0.45% by weight surfactant.

14. The system according to claim 1 wherein the composition is capable of producing a spray pattern in the absence of sputtering when sprayed.

* * * * *